United States Patent [19]

Ivany

[11] Patent Number: 4,621,648
[45] Date of Patent: Nov. 11, 1986

[54] ANKLE SUPPORT SYSTEM
[76] Inventor: Michael Ivany, 1120 S. Pine Creek Rd., Fairfield, Conn. 06430
[21] Appl. No.: 745,377
[22] Filed: Jun. 17, 1985

Related U.S. Application Data

[63] Continuation-in-part of Ser. No. 635,002, Jul. 27, 1984, abandoned.
[51] Int. Cl.⁴ ............................ A43B 7/20; A61F 5/00
[52] U.S. Cl. ................................. 128/80 H; 128/166; 36/89
[58] Field of Search ................ 128/80 R, 80 D, 80 H, 128/80 J, 166, 166.5, 165, 153; 36/58.5, 58.6, 8.3, 11.5, 89-92, 113-115, 126-130

[56] References Cited

U.S. PATENT DOCUMENTS

| | | | |
|---|---|---|---|
| 892,152 | 6/1908 | Harman | 36/89 X |
| 1,351,248 | 8/1920 | Hill | 128/166 |
| 2,994,322 | 8/1961 | Cullen et al. | 128/80 |
| 3,028,861 | 4/1962 | Shapiro | 128/166 |
| 3,073,305 | 1/1963 | Biggs, Jr. et al. | 128/80 H X |
| 3,298,365 | 1/1967 | Lewis | 128/80 |
| 3,327,410 | 6/1967 | Park, Sr. et al. | 36/2.5 |
| 3,383,708 | 5/1968 | Pappas | 2/22 |
| 3,407,811 | 10/1968 | Stubbs | 128/166 |
| 3,490,450 | 1/1970 | Gardner | 128/166 |
| 3,506,000 | 4/1970 | Baker | 128/166 |
| 3,515,136 | 6/1970 | Baker | 128/166 |
| 3,527,211 | 9/1970 | Baker | 128/166 |
| 3,534,957 | 10/1970 | Norman et al. | 273/55 |
| 3,674,023 | 7/1972 | Mann | 128/166 |
| 3,721,237 | 3/1973 | Alessio | 128/149 |
| 3,735,758 | 5/1973 | Novotney | 128/82 |
| 3,777,751 | 12/1973 | Wise | 128/166 |
| 3,800,789 | 4/1974 | Schloss | 128/90 |
| 3,834,377 | 9/1974 | Lebold | 128/80 H |
| 3,970,083 | 7/1976 | Carrigan | 128/166 |
| 4,085,746 | 4/1978 | Castiglia | 128/166 |
| 4,133,311 | 1/1979 | Karczewski | 128/166 |
| 4,166,460 | 9/1979 | Applegate | 128/80 H |
| 4,200,997 | 5/1980 | Scheinhaus et al. | 36/11.5 |
| 4,236,328 | 12/1980 | Friedlander | 36/58.5 |
| 4,237,874 | 12/1980 | Nelson | 128/80 H |
| 4,280,488 | 7/1981 | Polsky et al. | 128/80 H |
| 4,280,489 | 7/1981 | Johnson, Jr. | 128/80 H |
| 4,289,122 | 9/1981 | Mason et al. | 128/80 E |
| 4,313,433 | 2/1982 | Cramer | 128/80 H |
| 4,323,058 | 4/1982 | Detty | 128/80 H |
| 4,367,733 | 1/1983 | Stromgren | 128/166 |
| 4,378,793 | 4/1983 | Mauldin et al. | 128/80 H |
| 4,409,976 | 10/1983 | Pence | 128/166 |
| 4,411,077 | 10/1983 | Slavitt | 36/89 |
| 4,459,980 | 7/1984 | Perser et al. | 128/80 E |
| 4,461,288 | 7/1984 | Curtis | 128/80 H |
| 4,489,719 | 12/1984 | Lapenskie | 128/80 H |
| 4,495,942 | 1/1985 | Palumbo | 128/80 H |

FOREIGN PATENT DOCUMENTS

| | | |
|---|---|---|
| 241330 | 11/1911 | Fed. Rep. of Germany ...... 128/166 |
| 323107 | 7/1920 | Fed. Rep. of Germany ...... 128/166 |
| 511968 | 11/1930 | Fed. Rep. of Germany ... 128/80 H |

OTHER PUBLICATIONS

Page 126 of F. Sammons, Inc., 1983 Catalog showing an "Ankle-Based Toe Lifter".

*Primary Examiner*—Clifford D. Crowder
*Attorney, Agent, or Firm*—William G. Rhines

[57] ABSTRACT

An ankle support system is provided which comprises an ankle brace portion removeably attached to the user's foot and a strap support portion attached to the user's shoe and including one or more straps, said one or more straps being connected to the ankle brace portion during use and being of a length which will: (1) restrain the joint from overextension, and (2) provide relatively unimpeded motion of the ankle joint through its normal range of motion. In certain preferred embodiments of the invention, the strap support portion includes a first strap and a second strap, both of which are attached to the same side of the user's shoe, the first strap being wrapped around the lower part of the user's leg after first having passed around the back of the user's foot, and the second strap passing around the back of the user's foot after first having passed over the top of the user's shoe.

The free ends of the straps may be removeably affixed, as by means of "Velcro", to an ankle brace member in the form of a laced inner-shoe or, preferably, a Velcro sleeve wrapped around the leg just above the ankle bone, with the straps counter-directionally wrapped about the lower extremity.

14 Claims, 9 Drawing Figures

ANKLE SUPPORT SYSTEM

This is a continuation-in-part of co-pending application Ser. No. 635,002, filed on July 27, 1984, now abandoned.

BACKGROUND OF THE INVENTION

1. Field of the Invention

This invention relates to an ankle support system and in particular to an ankle support system wherein the user can participate in vigorous athletic activities.

2. Description of the Prior Art

Overextension of the ankle joint, i.e., an over-inversion or over-eversion of the joint, is a particularly troublesome problem in sports such as tennis where participants change their direction of motion frequently. Such overextensions often result in severe traumatic injury to the ankle joint since they usually occur at a time when the player's full weight and momentum is being applied to the muscles, tendons and ligaments of the ankle. Once injured, long recovery periods are often required for the ankle joint to heal. Moreover, prior injuries of this type often make the ankle joint more susceptible to future injuries, and often such future injuries are more serious than the original injury.

A particularly insidious aspect of over-inversion or over-eversion injuries is the fact that they occur sporadically, often years apart, and usually without any prior warning. Accordingly, an orthopedic appliance directed at providing relief for this type of injury has to be one which the user will be willing to wear every time he participates in vigorous athletic activities; that is, it must be one which the user will perceive as not unduly interfering with the normal range of motion of his ankle joint. At the same time, the appliance must provide a high level of stabilization for the joint since, as discussed above, these injuries usually occur when high levels of stress are being applied to the joint.

The orthopedic appliances designed to date unfortunately have not been able to satisfy these twin requirements of high level stabilization and low level interference with the normal range of motion of the ankle joint. Typically, prior art appliances have been designed to supply a low level of support and thus are not capable of providing the protection needed to prevent overextension injuries. Although appliances are known which will immobilize the ankle joint in one or more directions, these appliances are designed for use during the acute phases of ankle injury, and are not suitable for long term use during vigorous athletic activity.

SUMMARY OF THE INVENTION

In view of the existing state of the art, it is an object of the present invention to provide an orthopedic appliance for the ankle joint which will provide a level of stabilization suitable to protect the joint from overextension injuries while at the same time providing a range of motion for the user's ankle joint which will allow him to participate in vigorous athletic activities. It is a further object of the invention to provide an ankle support system which is easy to use, inexpensive to produce, and long lasting.

To achieve these and other objects, the invention provides an ankle support system which comprises an ankle brace portion and a strap support portion. The ankle brace portion is removeably attached to user's foot; in certain preferred embodiments of the invention, it is in form of a lace-up ankle brace. In other preferred embodiments, the ankle brace portion may be in the form of any of a number of other structures that are also designed to be removeably affixable to the feet and/or lower portion of the legs in substantially fixed position, so as to provide an anchor for one end of the straps against which the tension of the straps may be applied without substantial migration of the brace in the direction of the tension force moments; thereby preventing the straps from becoming undesirably slack and/or the ankle brace from migrating down the leg. An example of another type of ankle brace which meets these criteria is an ankle cuff or collar in the form of a flexible strip, including end fastening means, made from material which may be extensible and soft in texture, as by being padded with foam layers, etc., that may be retainably affixed to the lower leg by wrapping it about the leg just above the ankle. Such a strip may include "Velcro" surfaces so as to render it universally adaptable to various leg sizes, to make it readily removeable and affixable, and to adapt it for affixation thereto of the free ends of the associated straps. All as hereinafter described. The strap support portion comprises one or more straps attached to the user's shoe.

In use, the straps are firmly attached to the ankle brace portion of the support system. The straps have a length which will: (1) restrain the ankle joint from overextension, and (2) provide relatively unimpeded motion of the ankle joint through its normal range of motion. More particularly, the straps have a length which does not significantly impact on the motion of the user's ankle joint until that motion begins to exceed the normal range of motion of the joint and thus becomes an overextension. At that point, the straps exert a maximal restraining force on the joint and thus prevent it from being overextended.

In certain preferred embodiments of the invention, the strap support portion includes two straps attached to the same side of the user's shoe. One of the straps (hereinafter strap "A") passes around the back of the user's foot and then is wrapped around the lower part of the user's leg. The other strap (hereinafter strap "B") passes over the top of the user's foot and then around the back of the user's leg; i.e., counter-directionally to strap A.

This preferred wrapping strategy has been found to provide overall protection against overextension, while still permitting essentially a full range of motion for the user's ankle joint. In addition, this strategy in combination with a lace-up ankle brace has been found to give the user a sense of confidence that his ankle joint is being protected and thus is not likely to be injured. This sense of confidence is particularly important for users who have previously had overextension injuries and still want to participate in vigorous athletic activities. Alternative strap arrangements may include more than two straps between each shoe and its associated ankle brace. In one such preferred arrangement, two straps are affixed to each side of the shoe, to provide even greater strength characteristics. Such arrangements are particularly useful in more active sports where advanced or professional athletes are making sudden or violent direction changes, such as in soccer, tennis, etc. When such additional straps are used all but one of them will be adapted for fastening on both top and bottom while the remaining one needs to be adapted for such fastening only on the bottom. The reason is that those which include fastening means on both sides may then be wound around the lower leg and anchored to the ankle brace in any sequential order, with assurance that each tape newly added will have means to be anchored to both the ankle brace and the outside of each tape which preceeded it in the winding process, while the last one to be applied does not need to have fastening means on its outer surface to adapt it for inter-fastening with any tapes other than those which have preceeded it in the process.

In other preferred embodiments, hook and pile type fastener material, of the type commonly known as "VELCRO" fasteners i.e., synthetic materials in complementary male and female forms which adhere to one another when pressed together, are used for attaching the strap support and ankle brace portions of the support system together. When used with the preferred wrapping strategy and lace-up ankle brace described above, male portions of the fastener are preferably placed on the inside of each of straps A and B and female portions are preferably placed on the outside of the ankle brace and on the outside of strap A. In this way, strap A becomes firmly attached to the ankle brace as it is wrapped around the lower portion of the user's leg, and strap B becomes firmly attached to strap A as it is wrapped around the back of the user's foot. Use of "VELCRO" fasteners allows for quick and easy application of the appliance and permits the user to adjust the appliance to fit his particular anatomy. Similarly, any other form of ankle brace, such as the ankle cuff or collar of the type previously described as comprising a strip to be wrapped about the lower leg just above the ankle, may be provided with such female Velcro fastening means to adapt it for removeable affixation thereto of male Velcro fastening constituents affixed to the inner end of the associated straps. Of course, in all instances, the foregoing will apply as well regardless of how many straps are being utilized.

The accompanying drawings, which are incorporated in and constitute part of the specification, illustrate the preferred embodiments of the invention, and together with the description, serve to explain the principles of the invention. It is to be understood, of course, that both drawings and the description are explanatory only and are not restrictive of invention. In particular, although use of invention to restrain ankle joint from over-inversions is illustrated in the drawings, it is to be understood that invention is equally applicable to over-eversion problems, in which case strap support portion of support system is attached on the inboard, rather than the outboard, surface of the user's shoe. Also, the invention can be used to restrain simultaneously the ankle joint from both over-inversions and over-eversions, in which case strap support portions are applied to both the inboard and outboard surfaces of the user's shoe. As such, one, or more than one strap as previously disclosed, may be applied to both the inboard and the outboard surfaces of the user's shoes.

DESCRIPTION OF THE PREFERRED EMBODIMENTS

Figure 1:
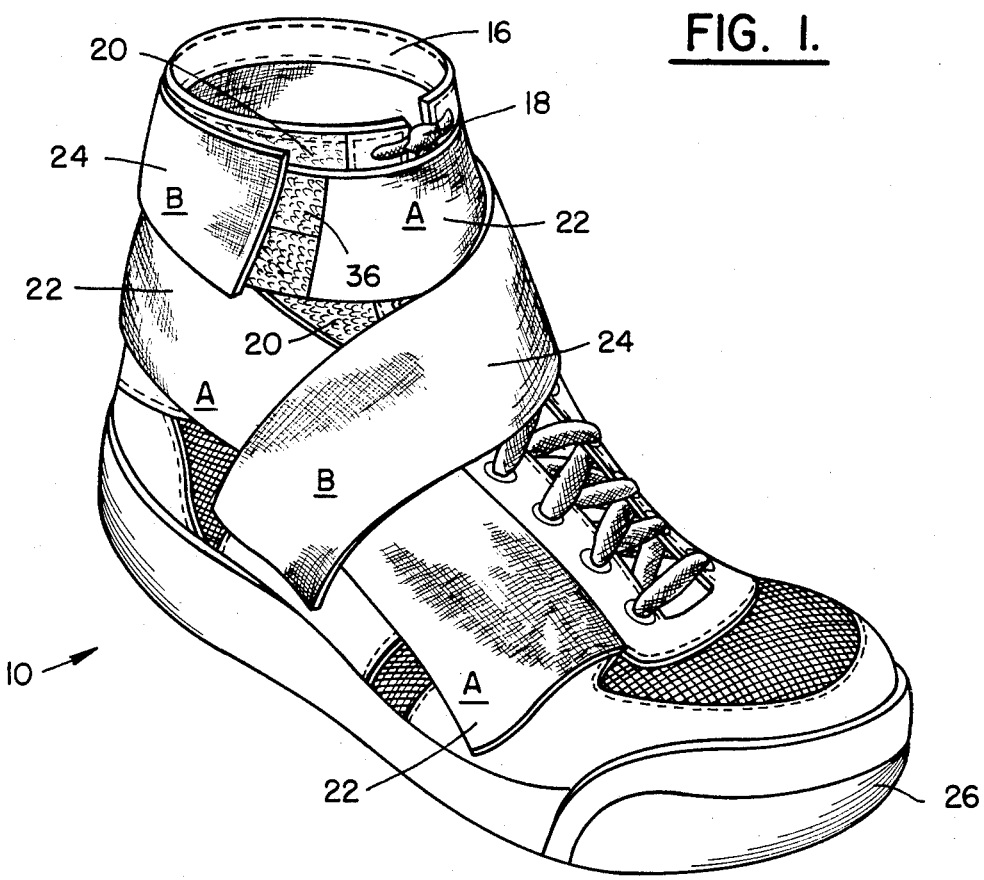
FIG. 1 is a perspective view of the ankle support system of the present invention as applied to a user's right foot.
Figure 2:
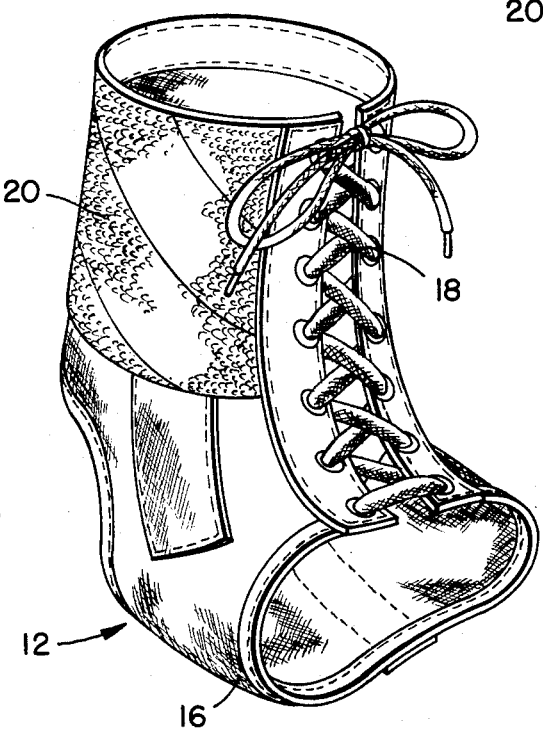
FIG. 2 is a perspective view of the ankle brace portion of the support system of FIG. 1.
Figure 4:
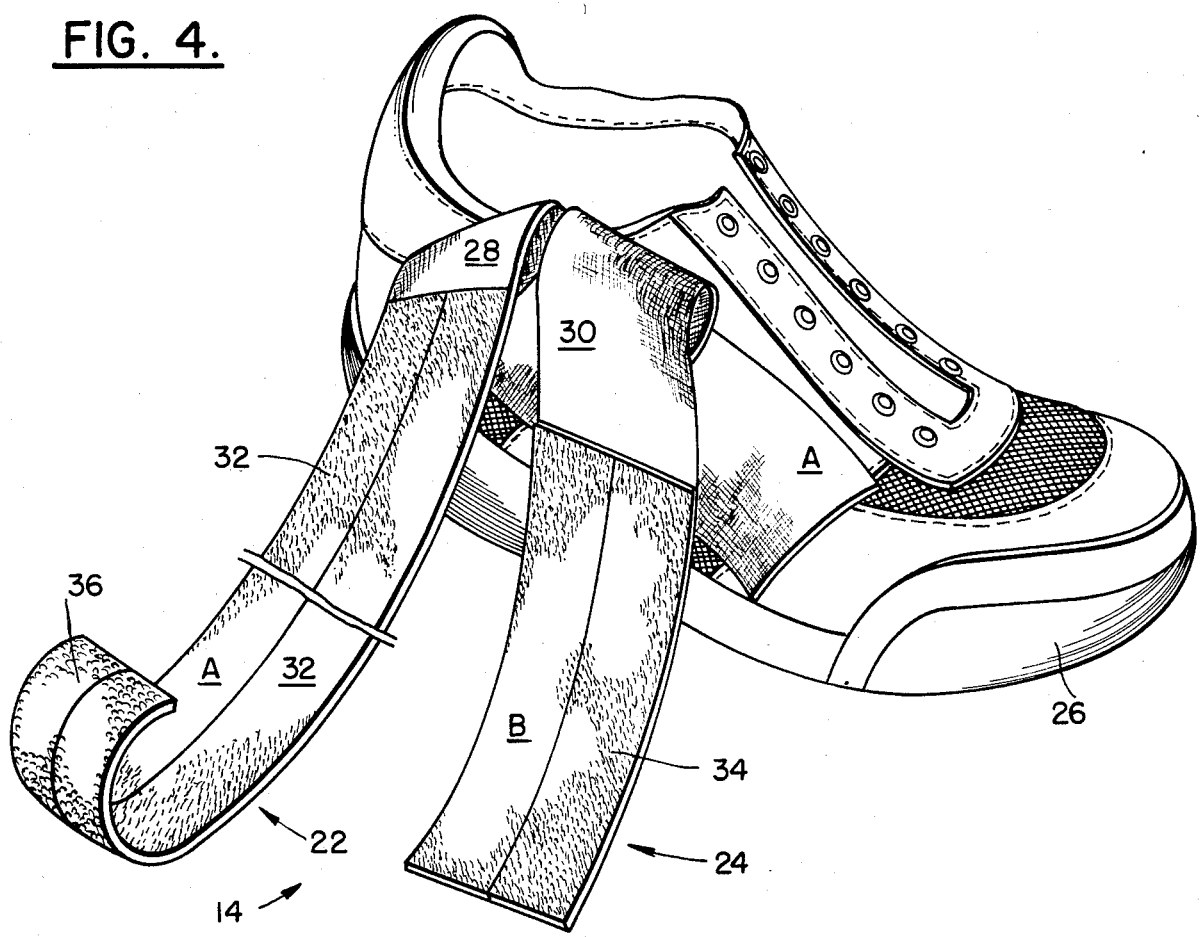
FIG. 4 is a perspective view of the strap support portion of the support system of FIG. 1.

Referring now to the figures, FIG. 1 shows a perspective view of the overall ankle support system 10, while FIGS. 2 and 4, respectively, show perspective views of the ankle brace portion 12 and the strap support portion 14 which together make up the overall system.

Figure 3:
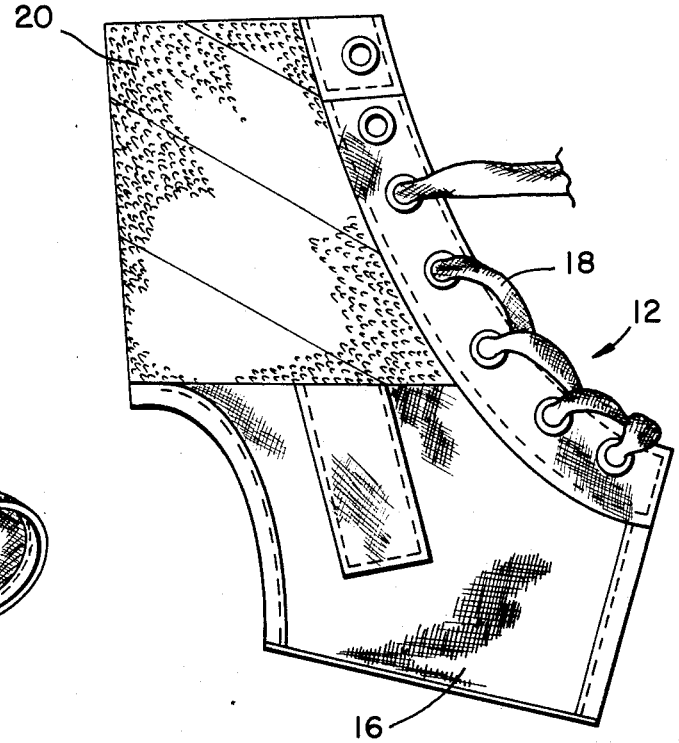
FIG. 3 is a side view of the ankle brace portion of the support system of FIG. 1.

As illustrated most clearly in FIGS. 2 and 3, the ankle brace portion preferably consists of a lace-up ankle brace 16 of conventional design. This brace is easily attached to user's foot and can be adjusted to produce a firm fit by means of laces 18. For attachment to strap support portion 14, brace 16 includes a female "VELCRO" pad 20 which covers the upper portion of the outside surface of brace.

As illustrated in FIG. 4, strap support portion 14 preferably includes straps A and B identified by the reference numerals 22 and 24, respectively. The straps are connected to user's shoe 26 by, for example, being stitched thereto.

Figure 7:
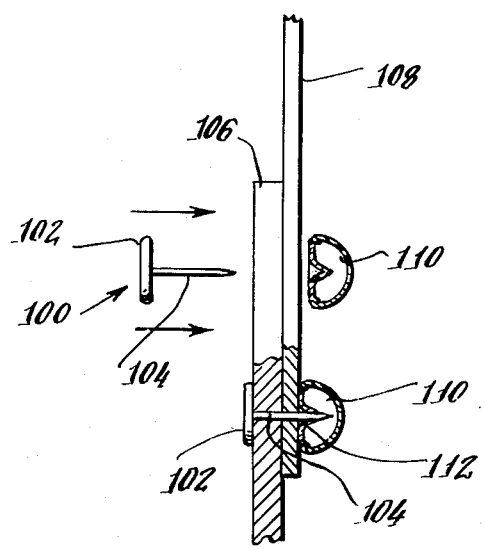
FIG. 7 is a cross-sectional view of an embodiment of this invention showing tack-button means for affixing straps to shoes.

Of course, any other suitable means may be employed to affix the shoe-end of the strap to the shoe, such as adhesives, rivets, staples, or the like. One alternative means that has been found to be particularly advantageous is shown in FIG. 7. It is in the form of a "Tackbutton" so-called, comprising a tack-like member 100 have a thin, flat metal head 102 and a pointed shaft 104 oriented at right angles to the head, and an associated tack button 110. With a strap 108 held in abutting juxtaposition to the outside of the shoe wall 106, the shaft 104 tack 100 may be pushed through the shoe wall 106 and the tack button 110 slipped over the pointed end of the tack shaft 104 to retainably secure the tack, the strap, and the shoe wall together. The structure and co-operation of the tack button 110 with the end of the shaft 104 on tack 100 is known per se, and is shown in the same figure. The depicted cross-section of the tack button shows that the inside of each tack button has inwardly oriented opposing tines 112 which permit the tack shaft end to be thrust into position between them but thereafter prevent the tack shaft 102 from backing out. An alternative which in some cases is desirable is to position the strap ends on the inside of the shoe rather than on the outside, as this offers appearance advantages.

Many advantages result from the use of such tack button fasteners. It is possible to market the straps and fasteners as a unit, so that they may be obtained as a kit and applied to the shoes by the user rather than having to be attached to the shoes during manufacture. As such, when more than one strap is to be used on either or both sides of a shoe, the straps in each set may be positionally affixed with respect to each other as an aid to the user in installation as well as in performance. Thus, it has been found that this invention performs well when two straps on a given side are oriented with respect to each other with an interior angle of 50° to 120°, and preferably of about 70°. These angular orientations facilitate making counter-directional wrappings of the straps about the legs, without "buckling" one edge of any of the straps. Such angular dispositions are easily and permanently fixed by so providing them to the user, but at the same time the user has all of the features which flow from the straps not having to be manufactured as part of the shoe itself. If a kit is provided for two straps per shoe and if velcro is to be used as the fastener, one in each pair would have male velcro on the inside, and female velcro on the outside, while the other would have only male velcro on the inside. If there are to be more than two straps per shoe, all but one would have male velcro on the inside and female velcro on the outside, while only one would have only male velcro on the inside only.

Another advantage of the methods of installation such as the tack-buttons previously described, is that they can be customized as to length to accomodate varying ankle sizes, the use of shin-guards, and other factors affecting the circumference about which the straps may be wrapped. Of course, it is possible to supply straps of long standard lengths and preferably of non-raveling material, so that they may be customized as to length by the user himself by cutting off and throwing away such excess as he does not need to accomodate his own wraparound length requirements. Further, with attachable straps as described, it is possible to change straps in the event the shoes or the straps wear out. In addition, they may be used with any shoes without requiring the shoes to be specially manufactured, thus improving the economics of their use.

The straps are preferably made of a non-elastic material so that they will provide a level of stabilization sufficient to restrain ankle joint from overextension. Materials having some elasticity can be used provided they will not stretch to a length which would correspond to an overextension of the user's ankle joint.

In practice, it has been found convenient for straps A and B to have lengths of approximately 18 and 12 inches, respectively. Strap A is made longer than strap B so that it can be wrapped around the lower portion of the user's leg. The 18 and 12 inch lengths are appropriate for support systems to be used by average adult males. Short lengths can be used for women and children, and longer lengths can be used when necessary.

Male "VELCRO" pads 32 and 34 are applied to the inside surfaces of straps A and B, respectively. In addition, a female "VELCRO" pad 36 is applied to outside surface of strap A. In use, male pad 32 on strap A adheres to female pad 20 on ankle brace 16, and male pad 34 on strap B adheres to female pad 36 on strap A.

Figure 6:
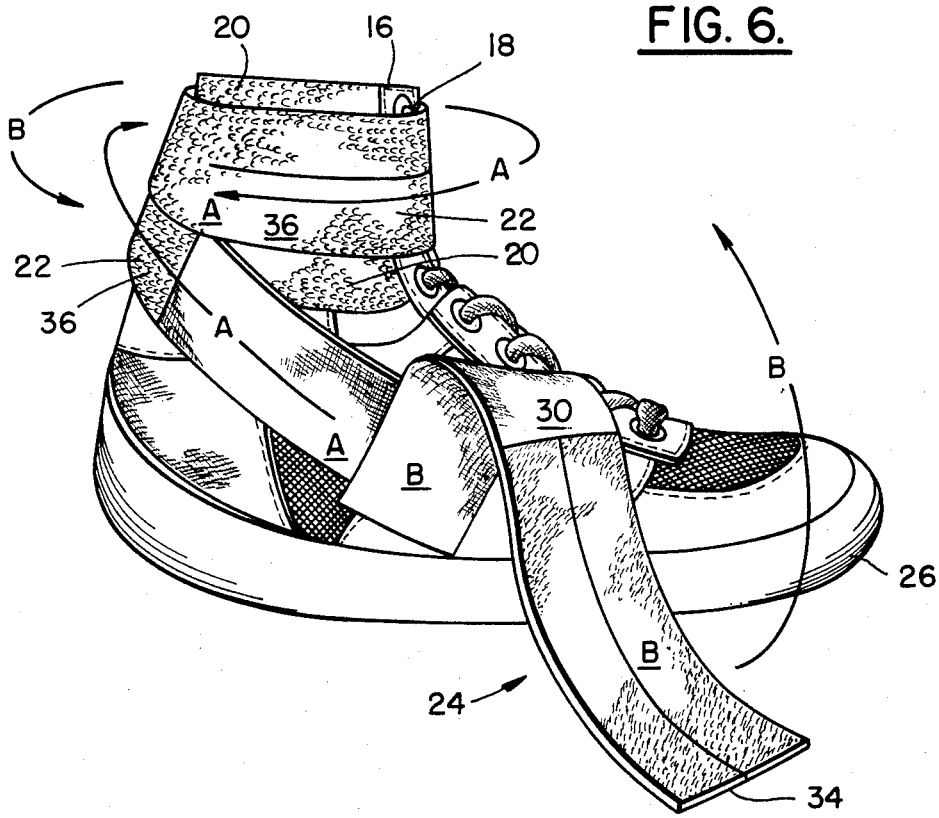
FIGS. 5 and 6 are perspective and side views, respectively, showing a preferred winding pattern for the strap support portion of the support system of FIG. 1.
Figure 5:
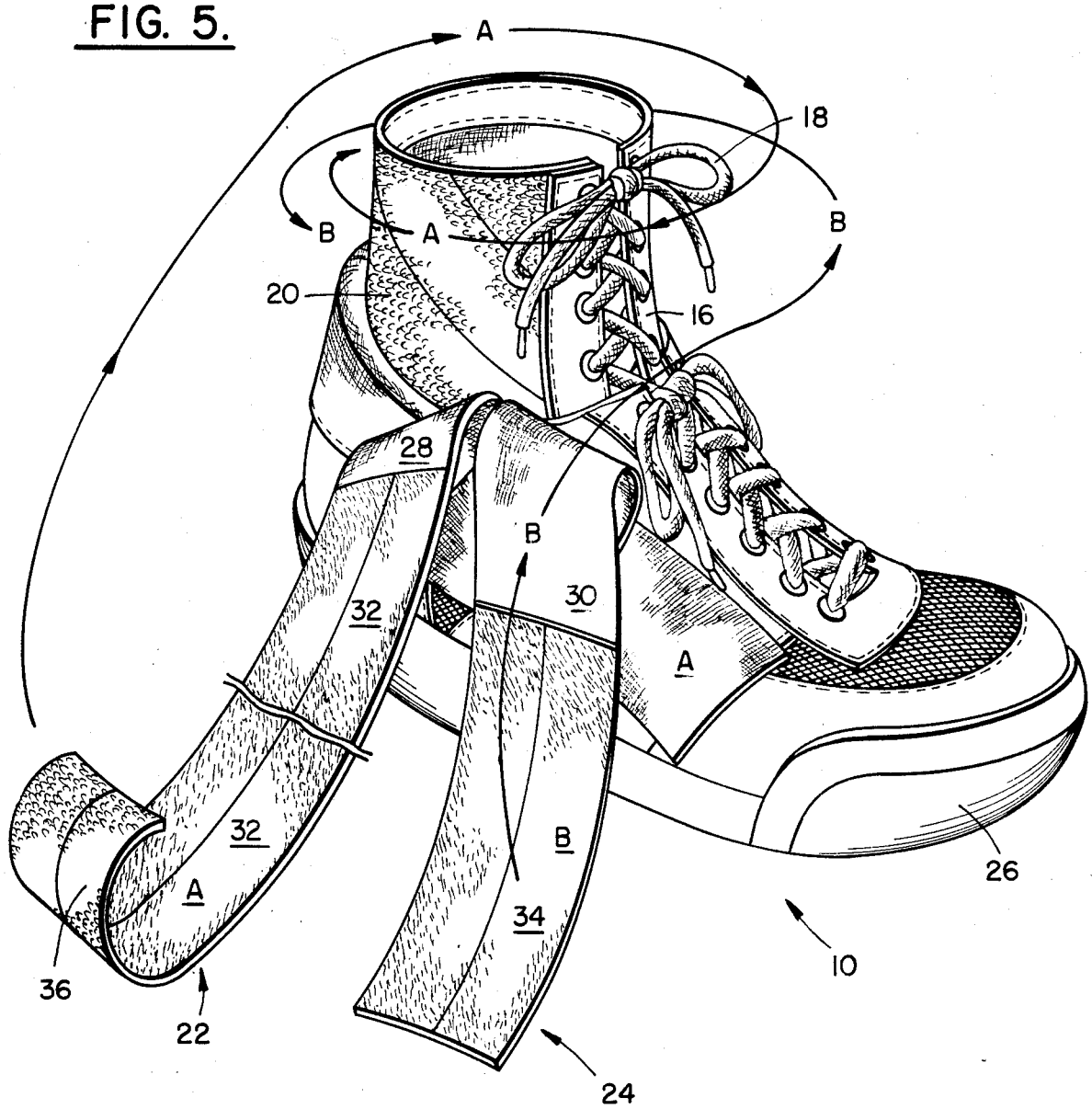

The ankle support system of this embodiment of present invention is employed by the user as follows. First, the user places lace-up ankle brace 16 on his foot and tightens laces 18 until a firm fit between the brace and the user's foot is achieved. The user then inserts his foot into his shoe and applies the strap support portion 14 of the overall system following the strap winding pattern shown in FIGS. 5 and 6. Specifically, in accordance with this pattern, the user first applies strap A by passing it around back of his foot, wrapping it clockwise (viewed from the top) around the lower part of his leg, and securing it to brace 16 by means of male "VELCRO" pad 32 on the inside of strap A and female "VELCRO" pad 20 on the outside of brace 16. Finally, the user applies strap B by passing it over the top of his shoe and counter-clockwise (when viewed from the top; i.e., counter directionally to strap A) around back of his foot, and then securing it to strap A by means of male "VELCRO" pad 34 on the inside of strap B and female "VELCRO" pad 36 on outside of strap A.

The installation process is quick and easy to perform, and by means of laces 18 and "VELCRO" pads 20, 32, 34, and 36, a custom fit is readily achieved by the user.

Figure 8:
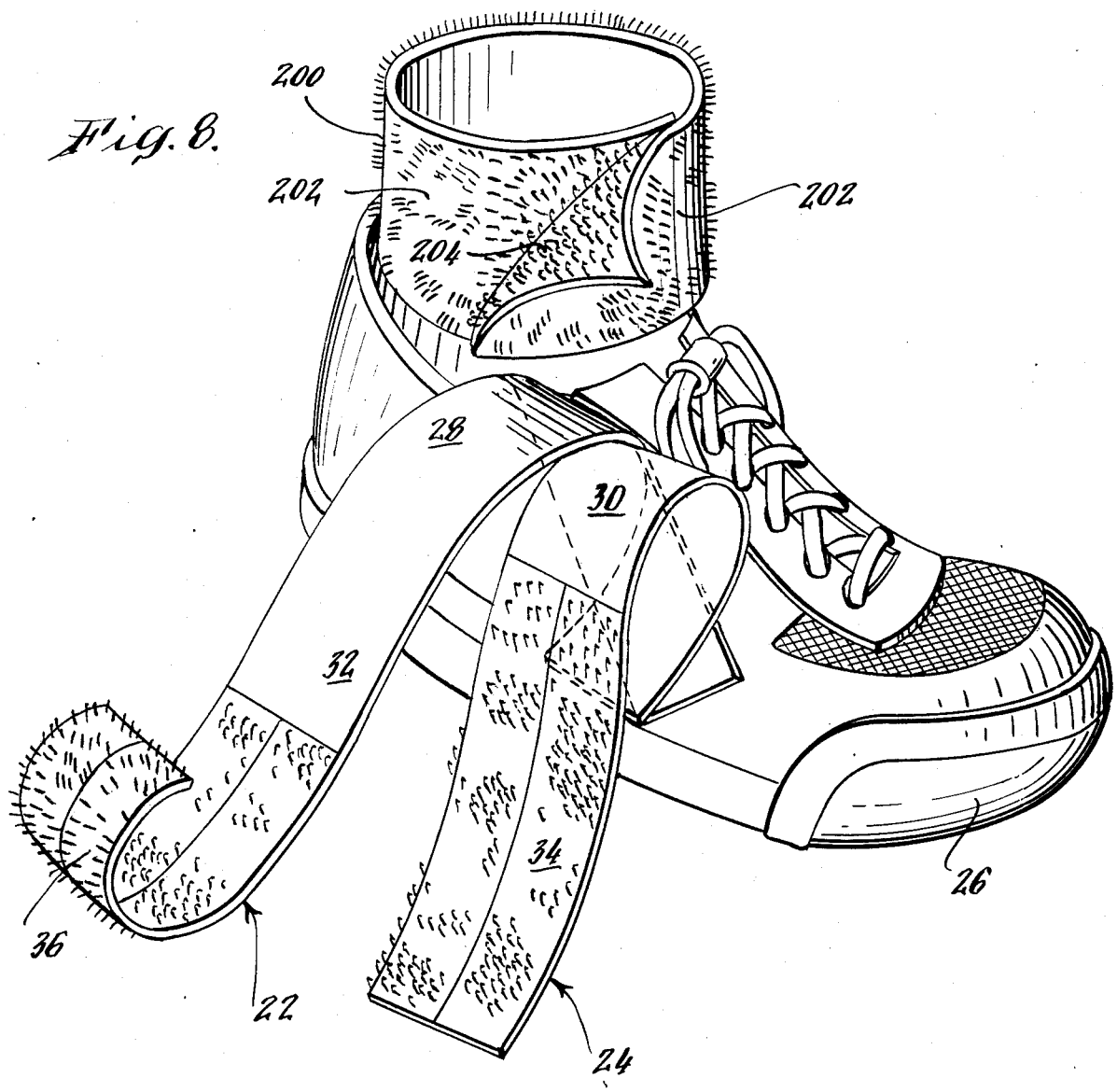
FIG. 8 is a perspective view of another embodiment of the present invention showing an ankle brace useful in the practice of this invention.

It has previously been noted that ankle braces structured other than as shown in FIG. 2 may also be used in embodiments of this invention, provided they are removeably affixable to the lower leg and/or foot and are so positioned and configured as to provide an anchor for the outermost ends of the straps against stress moments of force applied to the straps. One such preferred alternative ankle brace is illustrated in FIG. 8. It shows a shoe 26 have straps 22, 24 affixed thereto, substantially in the manner and with the associated structural elements illustrated in FIG. 4. However, as shown in FIG. 8, the ankle brace is of different structure than that shown in FIGS. 1, 2, 3, and 5. The ankle brace shown in FIG. 8 consists of a strip of textile material 200 which may be somewhat stretchable to assist it to conform to the contours of the lower leg. Preferably, it includes padding or an inner layer or underlayer to make it more comfortable to the user when in use. It also includes means for fastening the outer end in place once it has been wrapped around the lower leg, as well as means by which the free ends of the straps 22, 24 may be removeably affixed to the ankle brace 200. One preferred means for accomplishing these objectives is to use female velcro 202 to cover all of the exposed portion of the ankle brace strap at least once it is positioned on the user's leg, plus enough of the portion covered by the outermost end of the ankle brace strip to enable a corresponding male velcro strip 204 positioned on the inside of the outermost end of the ankle brace strip to be removeably affixed thereto. Preferably, although the entire outer surface of the ankle brace strip may be covered with female velcro fastener material, only the free end portion of its entire inner surface is covered with male velcro fastener material. This ensures good interconnection of each layer of the strip with each of its adjacent layers, and that there will be an ample and properly located outer female fastener surface to accomodate virtually any desired positioning of the strap ends affixed thereto, while, at the same time, the unwanted bulk that would result if male material were used throughout is avoided. In this context, the bulk may be further reduced by isolating the material to those areas where, when the straps are in position, male and female connector materials will be correspondingly juxtaposed to each other.

Figure 9:
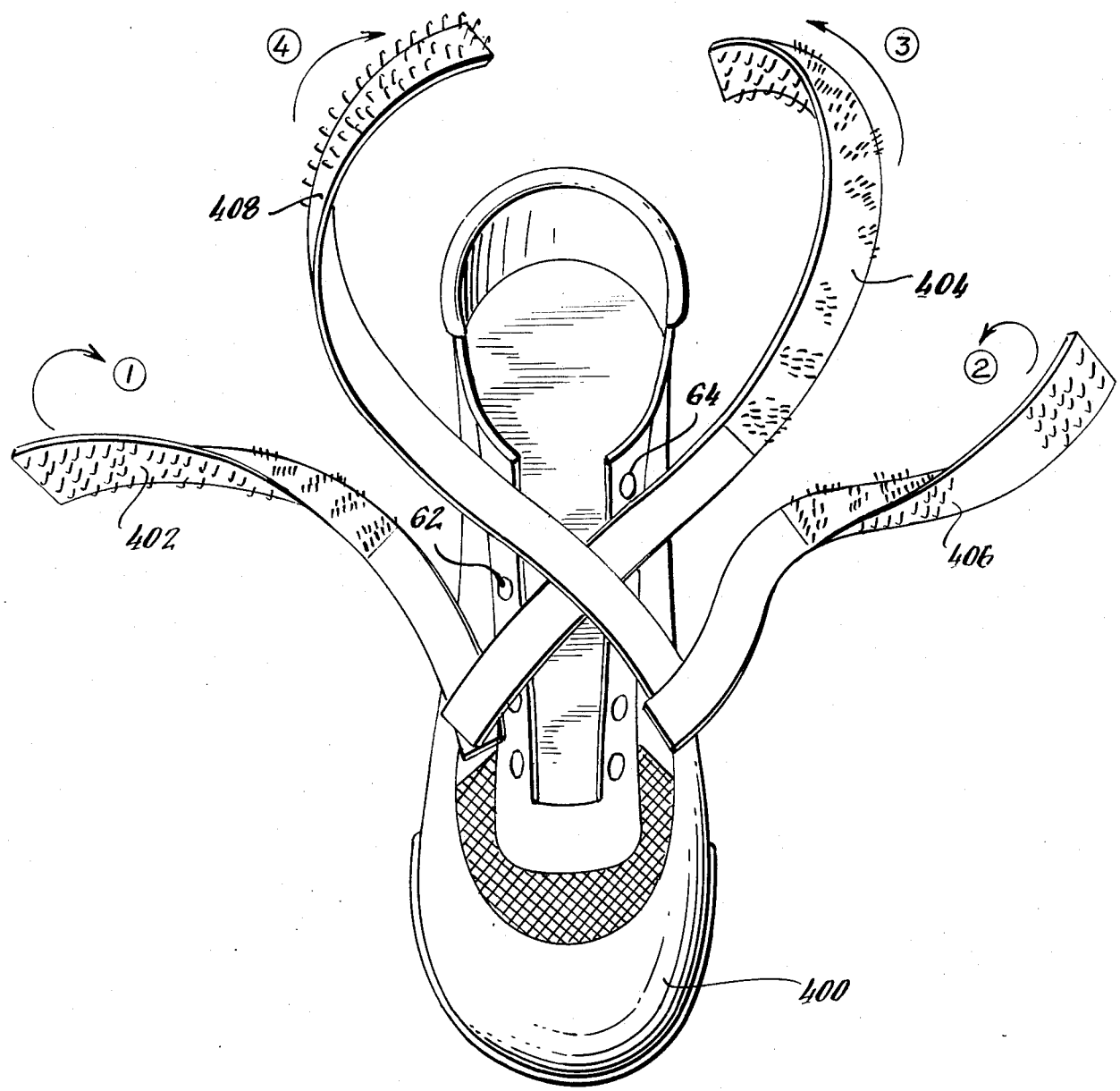
FIG. 9 is a perspective view of another embodiment of the present invention as applied to the user's right foot.

It has previously been noted that it is desirable in some instances to use a double set of straps on each side of each shoe. Such an arrangement is illustrated in FIG. 9. It shows a shoe 400 with a pair of straps 402, 404 affixed to one side of the shoe. This pair, like the pair 406, 408, may be configured with respect to each other as are the straps shown in FIGS. 3 through 6 inclusive. The second pair of straps 406, 408 is affixed on the opposite side of the shoe. Obviously, instead of two straps on one of the shoe sides, a single strap might also be used. Regardless of what total number of straps is used (that is, whether it is two, three or four), it is desirable for them to be adapted for removeable affixation to each other. Thus, if velcro is being used as the fastener material, it is desirable for all but one of the straps to have female velcro on the outside for connection to male velcro members on the inside of the straps as they are laid up on each other in successive layers. While female velcro on the outside of the strap which is to be in the outermost of the successive wrapped layers probably does no real harm, and will permit the straps to be applied in any sequential order, it would add to the costs of manufacture and perform no active fastening function and therefore is unnecessary and undesirable to use. The underside of each strap would include male velcro members, to permit removeable affixation of the bottom-most strap to correspondingly positioned female velcro on the outside of the ankle brace, as well as removeable affixation of each of the other straps to the strap that is beneath it as they are layed up upon each other in successive wound layers about the lower leg and/or foot.

FIG. 9 shows, by the arrows (1), (2), (3), and (4), a wrapping sequence that it is in accordance with this invention. Thus, as shown, if one were looking down at the top of the foot, the succession of strap wrapping about the lower leg and/or foot would be first strap 402 clockwise, then strap 406 counter-clockwise, then strap 408 clockwise, and finally strap 404 counter-clockwise. If that is the sequence to be followed and velcro is being used as the fastener, all of the first three straps that are successively wrapped (i.e., 402, 406, and 404) would have male velcro on the inside and female velcro on the outside, while the last strap to be layered up (i.e., strap 408) needs only to have male velcro on its inside surface. It should be noted that in such an arrangement, the exact sequence in which the straps are wound on each other usually is not critical, since no matter what sequence is followed, the net effect of at least some of them being counter-directionally laid up with respect to the others, is to create an effective stress lattice.

In each embodiment of this invention as previously disclosed, the result of having the straps affixed at one end to the shoe and at the other end to the ankle brace (albeit with having wound it about the ankle brace) is to have created such a stress lattice. As used in this context, the expression "stress lattice" is intended to mean a lattice in the structural sense that is designed to withstand stress moments of force on its constituent members. That is to say, in the aggregate, it is a group of two or more crossing straps which form a network which, while being individually flexible to moments of force directions other than that of linear extension, are also resistant individually to stress moments of force in the direction of linear extension and, in the aggregate, permit movement in only a few directions selected from among the several in which moments of force might be applied.

Thus, from this standard, it will be seen that with embodiments of the present invention as they are applied to the disclosed structures for application to the human leg and foot, by affixing the straps to the shoe walls farther toward the toe, the stress lattice as hereinbefore defined may be made to prevent the foot from toeing downward past a pre-determined point, as well as from rolling under in either direction, while permitting the ankle and therefore the foot to bend upward so as to facilitate running. Usually, however, downward as well as upward mobility of the toe is desired, while rolling under of the foot in either direction is to be prevented, so the configuration that has been depicted is the one which normally will obtain. As previously noted, the addition of straps increases the strength and/or the directional limitations against movement in undesired modes.

It is to be noted that there seem to be marked improvements in terms of positional stability in the results achieved with the present invention which utilizes an associate ankle brace, as compared to those achieved by merely wrapping velcro backed strap ends about the lower leg-ankle region. Absent an ankle brace, such as a collar, the first strap to be applied has nothing to be anchored to, and so must be wrapped so tightly in order to give it positional stability that loss of blood circulation and uncomfortable pressure on the Achilles tendon result. The positional stability that must be achieved in order to anchor the strap ends properly is not only against sliding downward over the ankle bone, but is also against the closed loops of the strap free ends rotating around the lower extremity. In a sense, with the anchor loop positioned about the lower leg, whether by overlaying the strap ends or by an ankle brace such as the collar previously described each strap coming up from the shoe which intersects the loop under tension at an angle, may be viewed as describing a resultant of forces having a vertical-downward component and a horizontal torqueing or revolving moment of force on the ankle brace. Without intending to be bound by any theory, it is believed that the difference in performance of the two systems may be explained as follows. Whether an ankle brace such as a collar, or a wraparound of straps ends is used, the constituent material must be sufficiently non-stretchable and the diameter of the closure about the lower leg sufficiently small to ensure that through operation of vertical-downward forces, the encircling collar will not simply slide down over the ankle. However, when an ankle brace is used, it appears not to need to be as tightly wrapped as do the strap ends in order to impart effective stability against movement horizontally to cause it to revolve about the lower leg. It is believed this difference may be attributable to the fact that with an overlay of strap ends to form the encircling collar, an amount of overlay of the end of the first strap sufficient to fix it upon itself builds the circumference of the outside of the collar thus formed to a diameter which is substantially greater than that of its inside. Then, the next strap is overlayed over the collar thus formed. This means that if equal tension is applied to both straps simultaneously, the second to have been applied will exhibit a greater mechanical advantage than will the first because, by analogy to a belt pulling on a sheave or a chain on a sprocket, the force applied is to a larger radius and therefore to a longer lever arm. The effect, therefore, is to cause the collar to rotate in the direction of the outermost or later-applied strap. This imbalance is exascerbated by the fact that while tension on the second-to-be-applied strap causes it to adhere more firmly to the outside of the underlying collar, tension on the first strap (which underlies the collar rather than overlying it) causes it to tend to pull out of disengagement with the interior of the collar, thus introducing some slackening and therefore effectively extensioning of the first strap. The result is that the collar is more free to revolve about the lower leg, with consequent loosening of the strap (which may even be disproportionate as between them), and associated reductions in the ability of the structure to resist stress on the strap and to prevent the foot from turning under. As noted above, extreme tightening of the strap ends forming the collar may inhibit this, but only with secondary constrictive effects that are not tolerable as a practical matter. All of this is to be contrasted with the use of an ankle brace of the type herein disclosed. Particular reference will be had to the collar-type ankle brace previously described, because it provides a clear basis for what is being said. This type of ankle brace must be sufficiently tight about the lower leg above the ankle that, being substantially non-extensible, it will not slide down over the enlargement formed by the ankle bones. To achieve this however, it need not be as tightly wrapped about the lower leg as strap ends forming a collar have to be, thereby providing a support member that is more comfortable and less constrictive to the circulatory system and the achilles tendon. Apparently these advantages are possible because both of the straps contact the outer surface of the ankle brace, and at little substantial difference in layer level, rather than the first strap contacting the inside of the "collar" formed by wrapping strap ends on themselves. As a result, tension applied simultaneously to two or more straps wrapped counter-directionally about the ankle brace will produce opposing torque moments of force on the ankle brace. As such, these torque moments will normally be substantially equal on average, particularly since (using again the analogy of a rope acting on a sheave or a chain acting on a sprocket) the strap tension is acting on lever arms of substantially equal length; the free strap ends all being affixed outside the collar, rather than the first among the group being affixed to the inside of the "collar" formed by the grouping of strap ends. As a result, there is less tendency for unevenness and/or slack to develop as between the constituent straps, with consequent effective limiting of any tendency of the foot to "roll-under".

Although specific embodiments of the invention have been described and illustrated, it is to be understood that modifications can be made without departing from the invention's spirit and scope. For example, other wrapping patterns and numbers of straps can be used for the strap support portion of the overall system, and braces other than lace-up braces can be used for the ankle brace portion. Similarly, fastening means other than "VELCRO" pads can be used for attaching the strap support portion to the ankle brace portion.

What is claimed is:

1. An ankle support system comprising an ankle brace portion adopted to be removeably attached to the user's foot and a strap support portion attached to the user's show which has left and right sides, said strap support portion including at least two straps, said straps being connected to the ankle brace portion during use with at least one of said straps wound about said brace portion counter-directionally to the other of said straps, and being of a length which will: (1) restrain the joint from over-extension, and (2) provide relatively unimpeded motion of the ankle joint through its normal range of motion.

2. The ankle support system of claim 1 wherein the strap support portion includes a first strap and a second strap, both of which are attached to same side of the user's shoe, the first strap being wrapped around the lower part of the user's leg after first having passed around the back of the user's foot, and the second strap passing around the back of the user's foot after first having passed over the top of the user's shoe.

3. The ankle support system of claim 2 wherein the first and second straps are connected to the ankle brace portion by means of pads of synthetic materials which adhere to one another when pressed together.

4. The ankle support system of claim 3 wherein the pads of synthetic materials have complementary male and female forms and wherein the first strap is connected to the ankle brace portion by means of a male pad on the inside surface of the first strap and a female pad on the outside surface of the ankle brace portion, and the second strap is connected to the first strap by means of a male pad on the inside surface of the second strap and a female pad on the outside surface of the first strap.

5. The ankle support system of claim 1 wherein the ankle brace portion is a wrap-around, self-adhering collar.

6. An ankle support system comprising an ankle brace adapted to be removeably attached to the user's foot and first and second straps attached to the same side of the user's shoe and connected to the ankle brace during use, the first strap being wrapped around the lower part of the user's leg after first having passed around the back of the user's foot, and the second strap passing around the back of the user's foot after first having passed over the top of the user's shoe.

7. The ankle support system of claim 6 wherein the first and second straps are connected to the ankle brace by means of pads of synthetic materials which adhere to one another when pressed together.

8. The ankle support system of claim 7 wherein the pads of synthetic materials have complementary male and female forms and wherein the first strap is connected to the ankle brace by means of a male pad on the inside surface of the first strap and a female pad on the outside surface of the ankle brace, and the second strap is connected to the first strap by means of a male pad on the inside surface of the second strap and a female pad on the outside surface of the first strap.

9. The ankle support system of claim 6 wherein the ankle brace is a wrap-around, self-adhering collar.

10. An ankle support structure comprising
an ankle brace member that is removeably positionable on the lower region of a human pedal extremity and is adapted for being retainably positioned there against downward directed moments of force applied thereto, and
at least two substantially non-extensible straps that are affixed to a shoe to be worn on the foot of said extremity,
means for affixing one end of each strap to said shoe,
said ankle brace member and said straps including means by which the other end of each of said straps, and said ankle brace member may be removeably affixed to each other with said other strap ends wrapped around said ankle brace after it has been positioned on said region with at least one of said straps oriented about said member counter-directionally about said brace with respect to the other of said straps, whereby, with said ankle brace positioned on said region and said straps so affixed to said shoe, the free ends of said straps may be so wrapped about said ankle brace and affixed thereto and to each other in successive layers to form a stress lattice to restrict movement of said foot with respect to its associated leg in selected directions.

11. The structure described in claim 10 wherein said ankle brace comprises a collar in the form of a flexible strip to be wrapped in at least one successive layer about the lower leg in the region immediately above the ankle bone, said strip including affixation means for removeably affixing the free end of said strip to the portion of said strip immediately beneath said end.

12. The structure described in claim 11 wherein said affixation means comprises hook-pile type fastener material.

13. A method of imparting selected positional stability to the foot comprising the steps of placing a shoe on the foot, positioning on the lower pedal extremity which includes the foot to be positionally stabilized, a removeable ankle brace which is adapted to be stabilized against downward movement along said extremity and is adapted for removeable affixation to it of the free ends of associated shoe straps, and positioning about said ankle brace in removeable affixation thereto the free ends of at least two straps, the opposite ends of which are affixed to said shoe positioned on said foot, with at least one of said straps counter-directionally oriented with respect to other of said straps and with said straps normally under tension, and thereby preventing further movement of said foot with respect to the associated leg, when said foot is so positioned that further movement of the foot with respect to the leg in the straps' tension-producing direction is desired to be prevented.

14. The method described in claim 13 including the step of affixing the end of each of said straps that is opposite its free end to the shoe with which it is to be associated.

* * * * *